(12) United States Patent
Wakamura

(10) Patent No.: US 8,080,214 B2
(45) Date of Patent: Dec. 20, 2011

(54) AIR CLEANER

(75) Inventor: Masato Wakamura, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 989 days.

(21) Appl. No.: 11/128,166

(22) Filed: May 13, 2005

(65) Prior Publication Data

US 2005/0201907 A1 Sep. 15, 2005

Related U.S. Application Data

(63) Continuation of application No. PCT/JP02/11985, filed on Nov. 15, 2002.

(51) Int. Cl.
*B01J 19/08* (2006.01)

(52) U.S. Cl. ...................................... 422/186.3; 422/121

(58) Field of Classification Search ................ 422/186.3, 422/121
See application file for complete search history.

(56) References Cited

U.S. PATENT DOCUMENTS

| | | | |
|---|---|---|---|
| 3,959,149 A * | 5/1976 | Oda et al. | 528/68 |
| 5,790,934 A * | 8/1998 | Say et al. | 422/186 |
| 5,909,613 A | 6/1999 | Miyoshi et al. | |
| 6,566,300 B2 * | 5/2003 | Park et al. | 502/350 |
| 6,653,356 B2 * | 11/2003 | Sherman | 516/90 |

FOREIGN PATENT DOCUMENTS

| | | |
|---|---|---|
| EP | 1112752 A2 | 7/2001 |
| JP | 64-11622 | 1/1989 |
| JP | 6-218234 | 8/1994 |
| JP | 8-266609 | 10/1996 |
| JP | 11-151443 | 6/1999 |
| JP | 11-285643 | 10/1999 |
| JP | 2000-202016 | * 7/2000 |
| JP | 8-266609 | 11/2000 |
| JP | 2000-327315 | 11/2000 |
| JP | 2001-253235 | 9/2001 |
| JP | 2002-66257 | 3/2002 |
| JP | 2002-253662 | 9/2002 |

OTHER PUBLICATIONS

Supplemental European Search Report dated Mar. 31, 2009 for a related European Application.

* cited by examiner

*Primary Examiner* — Kishor Mayekar
(74) *Attorney, Agent, or Firm* — Staas & Halsey LLP

(57) ABSTRACT

An air cleaner X1 includes a cleaning chamber (R2) through which air can pass, an ultraviolet light source (12) provided in the cleaning chamber (R2), a flow generator (11) for generating an air flow in the cleaning chamber (R2) by passing air through the cleaning chamber (R2), and photocatalyst granules (13) having a photocatalytic function, held in the cleaning chamber (R2), and displaceable by the air flow.

6 Claims, 4 Drawing Sheets

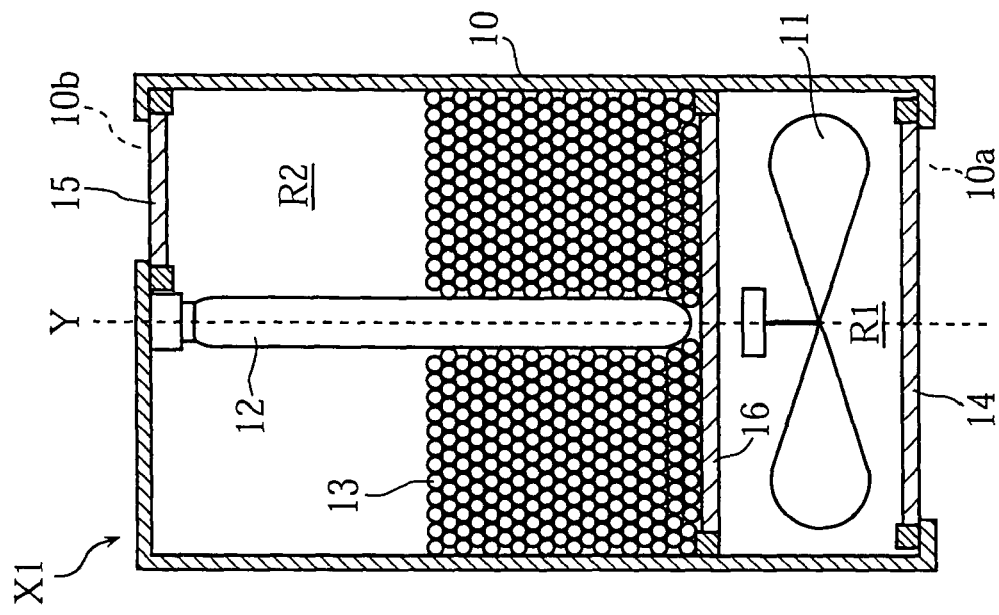
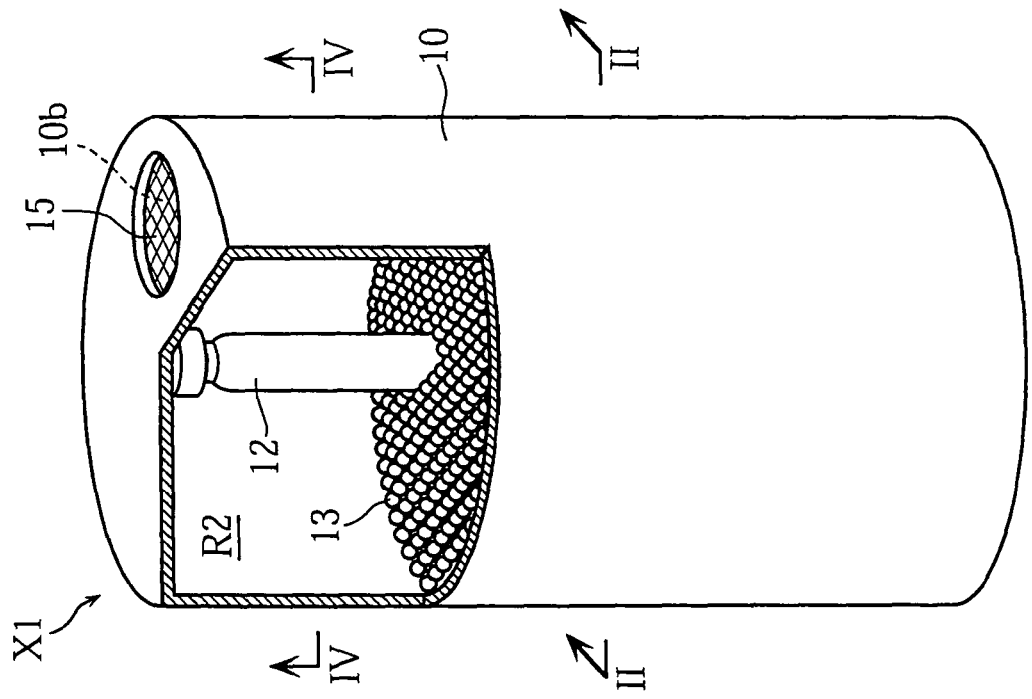

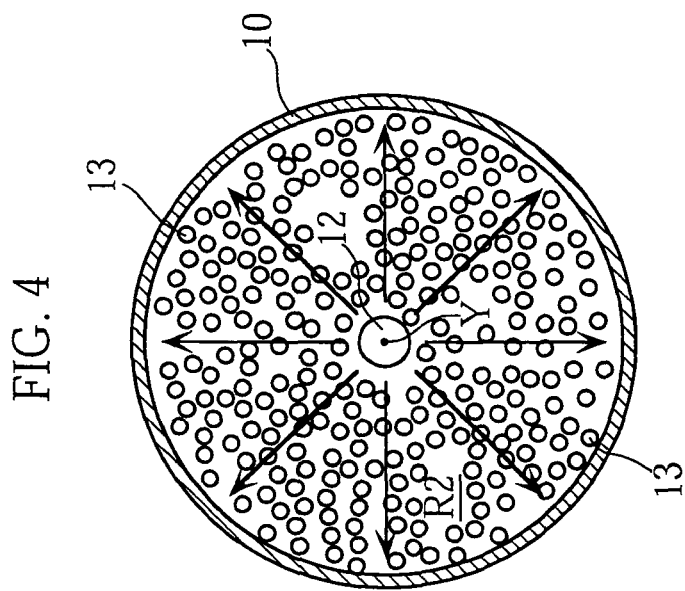
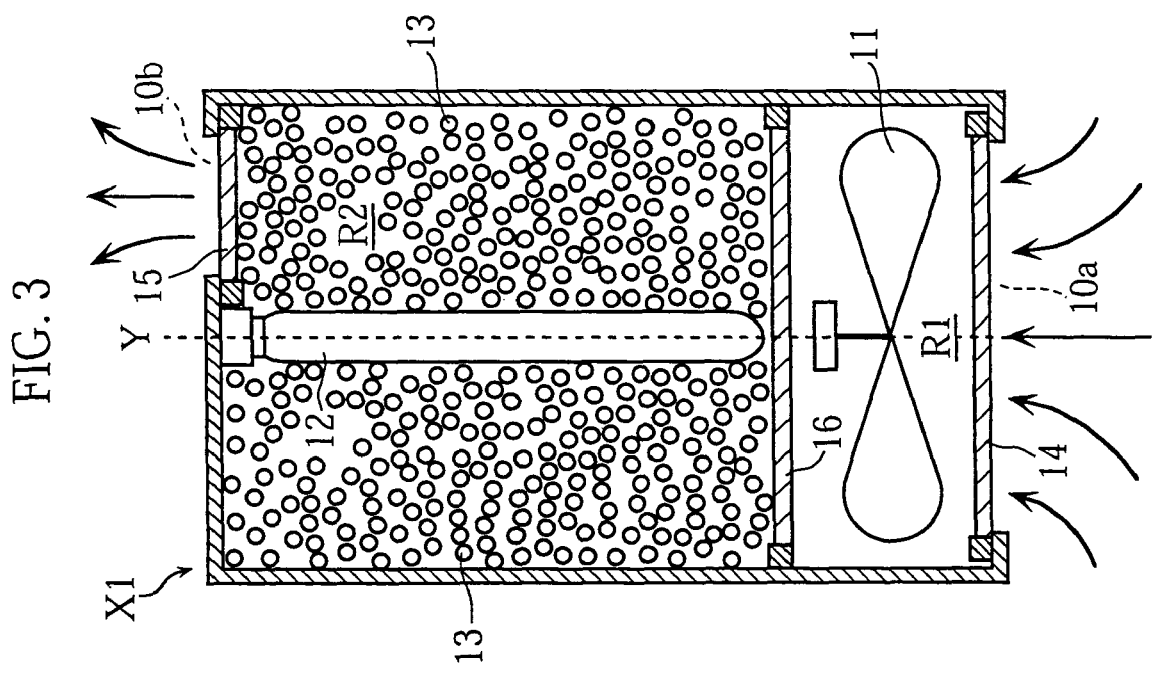

AIR CLEANER

This application is a continuing application, filed under 35 U.S.C. §111(a), of International Application PCT/JP2002/011985, filed Nov. 15, 2002, incorporated by reference herein.

TECHNICAL FIELD

This invention relates to an air cleaner for cleaning the air indoors and in vehicles, for example.

BACKGROUND ART

An air cleaner is sometimes used to clean, deodorize, or otherwise treat the air indoors and in vehicles, and particularly in closets, shoe cabinets, refrigerators, and kitchen cabinets. Air cleaners have been disclosed, for example, in JP-A 11-151443, JP-A 2001-253235, and JP-A 2002-253662.

There are known air cleaners that utilize a photocatalytic substance. Such air cleaners are have been disclosed, for example, in JP-A 11-151443 and JP-A 2002-253662.

FIG. 7 schematically illustrates a conventional air cleaner X2 that utilizes a photocatalytic substance. The air cleaner X2 comprises a housing 71, a dust filter 72, photocatalyst filters 73 and 74, an ultraviolet lamp 75, a fan 76, and a filter 77.

The housing 71 has an intake opening 71a and an exhaust opening 71b. The filter 72 is provided so as to block off the intake opening 71a, and the filter 77 is provided so as to block off the exhaust opening 71b. The photocatalytic filters 73 and 74 are composed of a nonwoven cloth to which powdered titanium oxide ($TiO_2$) has been bonded, and functions when irradiated with the UV lamp 75. The fan 76 is provided on the exhaust opening 71b side, and actuating the fan 76 causes air to pass through the air cleaner X2. More specifically, when the fan 76 is actuated, air flows through the intake opening 71a and into the air cleaner X2, passes through the filter 72, the photocatalytic filters 73 and 74, and the filter 77 in that order, and then is exhausted from the air cleaner X2 via the exhaust opening 71b. Some semiconductor substances, such as titanium oxide, are known to have a photocatalytic function. Semiconductor substances having a photocatalytic function generally absorb light having energy corresponding to the bandgap of the valence band and the conduction band, which causes the electrons of the valence band to migrate to the conduction band, and this electron transition produces holes in the valence band. The electrons of the conduction band have the property of moving to a substance adsorbed to the surface of the photocatalytic functional semiconductor, and as a result this adsorbed substance can be reduced. The holes in the valence band have the property of stealing electrons from the substance adsorbed to the surface of the photocatalytic functional semiconductor, and as a result this adsorbed substance can be oxidized.

With titanium oxide ($TiO_2$) having a photocatalytic function, the electrons that have migrated to the conduction band reduce the oxygen in the air and produce super-oxide anions ($•O_2^-$). Along with this, the holes produced in the valence band oxidize the adsorbed water on the titanium oxide surface and produce hydroxy radicals ($•OH$). Hydroxy radicals have an extremely powerful oxidation strength. Consequently, when an organic substance, for example, is adsorbed to photocatalytic titanium oxide, the action of the hydroxy radicals sometimes results in the organic substance being decomposed into water and carbon dioxide.

When the air cleaner X2 is operated, pollutants, microbes, and the like in the air are trapped in the photocatalytic filters 73 and 74. Since titanium oxide is adhered as a photocatalyst to the photocatalytic filters 73 and 74, as mentioned above, these pollutants, microbes, and so forth are subjected to a decomposing action in the photocatalytic filters 73 and 74 being irradiated with the UV lamp 75.

With this conventional air cleaner X2, the air has to be brought into contact very efficiently with the photocatalytic filters 73 and 74 in order to improve the air cleaning efficiency. This contact efficiency can be enhanced by increasing the surface area and/or thickness of the photocatalytic filters 73 and 74.

However, if the surface area of the photocatalytic filters 73 and 74 is increased, this tends to make the air cleaner X2 too bulky. Increasing the thickness of the photocatalytic filters 73 and 74 is also undesirable in terms of pressure loss when air passes through the photocatalytic filters 73 and 74. This is because when the thickness of the photocatalytic filters 73 and 74 is increased, there is a corresponding rise in the blower capacity required of the fan 76, and when the blower capacity of the fan 76 is raised, it is more difficult to keep the air cleaner X2 quiet.

Also, with the air cleaner X2, the amount of UV irradiation in the photocatalytic filters 73 and 74 is uneven. Specifically, the distance from the UV lamp 75 and the UV irradiation angle vary with the position on the photocatalytic filters 73 and 74. Accordingly, the decomposing action is insufficient in portions of the photocatalytic filters 73 and 74 where the amount of UV irradiation is small, and as a result, the intrinsic photocatalytic function had by the photocatalytic filters 73 and 74 cannot be fully realized with the conventional air cleaner X2.

The amount of UV irradiation can be made relatively uniform by increasing the number of UV lamps 75 installed, so it is possible to improve the photocatalytic function of the photocatalytic filters 73 and 74, and in turn to increase the air cleaning efficiency of the air cleaner X2. Nevertheless, with a configuration such as this, as the number of UV lamps 75 increases, so too does the number of inverters (not shown) needed to control the drive of these lamps and so forth, which ends up making the air cleaner X2 bulkier.

Thus, it was difficult to achieve high air cleaning efficiency while maintaining a small device size with the conventional air cleaner X2.

DISCLOSURE OF THE INVENTION

The present invention was conceived in light of this situation, and it is an object thereof to provide an air cleaner suitable for achieving higher air cleaning efficiency.

The air cleaner provided by the present invention comprises a cleaning chamber through the interior of which air can pass, an ultraviolet light source provided inside the cleaning chamber, an air flow generator for generating an air flow in the cleaning chamber by passing air through the cleaning chamber, and photocatalyst granules having a photocatalytic function, held in the cleaning chamber, and displaceable by the air flow. "Photocatalytic function" as used in the present invention refers to the function of catalyzing, under UV irradiation conditions, a reaction (such as an oxidative decomposition reaction) that changes the chemical structure of an organic substance, organic tissue, or the like. The photocatalyst granules having this function are composed, for example, of a powder made from a lightweight material such as a foamed resin, and a photocatalytic substance that is fixed to this lightweight powder. The displacement of the photocatalyst granules in the present invention refers to motion of the photocatalyst granules having a translational motion component and/or a rotational motion component. Displacing the photocatalyst granules means, for example, that the photocatalyst granules billow up.

The UV lamp or other UV light source and the fan or other air flow generator are actuated during the operation of an air cleaner with this constitution. The actuation of the air flow generator causes air to pass through the cleaning chamber, generating an air flow inside the cleaning chamber. The photocatalyst granules in the cleaning chamber are agitated by this air flow and billow up, for example. At this point, the photocatalyst granules are irradiated with UV light while the air passing through the cleaning chamber comes into contact with the photocatalyst granules, so any pollutants, microbes, or the like in the air are subjected to the catalytic action of the photocatalyst granules. When the photocatalyst granules are suitably in motion or billowing, the UV rays evenly hit the entire surface of the photocatalyst granules.

With the air cleaner of the present invention, since the UV rays evenly hit the entire surface of the photocatalyst granules, the photocatalytic function of the photocatalytic substance present on the surface of the photocatalyst granules is fully manifested. Since it is these granules that perform the air cleaning function in the air cleaner of the present invention, the contact efficiency between the photocatalytic substance and the air flow generator is higher per unit of volume than with a conventional air cleaner in which a filter performs the air cleaning function. Accordingly, the air cleaner of the present invention is suited to setting the air cleaning function per unit of volume higher. The air cleaning function or photocatalytic function per unit of volume can be adjusted by suitably adjusting the particle size or surface area of the photocatalyst granules and the packing ratio of the photocatalyst granules in the cleaning chamber. The motion or billowing of the photocatalyst granules can be suitably adjusted by adjusting the mass and shape of the photocatalyst granules and the packing ratio of the photocatalyst granules in the cleaning chamber.

The air cleaner of the present invention is thus suited to achieving a high air cleaning efficiency.

Preferably, the photocatalyst granules comprise carrier particles and a photocatalytic substance fixed to the carrier particles. The photocatalytic substance is preferably selected from the group consisting of photocatalytic apatite and titanium oxide.

When photocatalytic apatite is employed as the photocatalytic substance, this photocatalytic apatite is preferably titanium-modified calcium hydroxyapatite (Ti—CaHAP) having a chemical structure in which part of the calcium of calcium hydroxyapatite has been replaced with titanium.

A photocatalytic apatite such as this has been disclosed in Japanese Laid-Open Patent Application 2000-327315, for example, which discloses a photocatalytic apatite in which titanium oxide or another compound having a photocatalytic function and calcium hydroxyapatite (CaHAP) or another compound with an excellent ability to adsorb organic matter are compounded at the atomic level. More specifically, this photocatalytic apatite has a crystal structure in which some of the calcium constituting the CaHAP ($Ca_{10}(PO_4)_6(OH)_2$) is replaced with titanium, and a titanium oxide-like partial structure that is similar to the chemical structure of photocatalytic titanium oxide is formed at the places where this titanium is introduced. Since a titanium oxide-like partial structure capable of exhibiting a photocatalytic function is present within the crystal structure of CaHAP, which has excellent adsorption of organic matter, this effectively increases the contact efficiency between the titanium oxide-like partial structure and the organic matter or other substances to be decomposed. As a result, the titanium oxide-like partial structure is capable, through its photocatalytic function, of the efficient oxidative decomposition of pollutants, microbes, and the like in the air.

When titanium oxide is employed as the photocatalytic substance, it is preferably anatase titanium oxide. Anatase titanium oxide is known as a photocatalytic substance.

Preferably, the carrier particles are composed of a resin. Also, preferably, a light reflecting film is provided to the surface of the carrier particles, and the photocatalytic substance is fixed over the light reflecting film.

The packing ratio of the photocatalyst granules in the cleaning chamber is preferably from 50 to 80%, and even more preferably from 60 to 70%.

Preferably, the cleaning chamber is columnar in shape, having a main extension direction, and the ultraviolet light source extends axially in the main extension direction of this columnar shape. Even more preferably, the cleaning chamber is cylindrical in shape.

The air cleaner pertaining to the present invention preferably further comprises a dust filter through which air passes prior to flowing into the cleaning chamber.

The air cleaner pertaining to the present invention preferably further comprises turbulence generation means in the cleaning chamber.

BRIEF DESCRIPTION OF THE DRAWINGS

FIG. 1 is a partially cut-away oblique view of the air cleaner pertaining to the present invention;

FIG. 2 is a cross section along the II-II line in FIG. 1;

FIG. 3 illustrates the air cleaner during operation;

FIG. 4 is a cross section along the IV-IV line in FIG. 1;

BEST MODE FOR CARRYING OUT THE INVENTION

Figure 6:
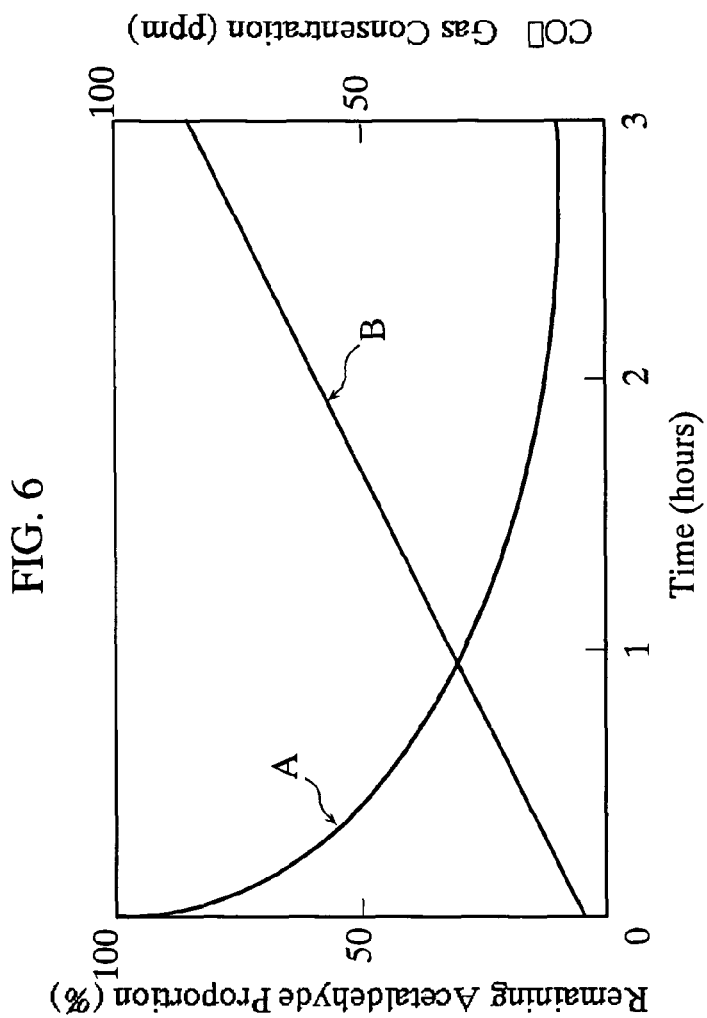
FIG. 6 is a graph of the measurement results in the working examples.

FIGS. 1 to 4 illustrate an air cleaner X1 pertaining to the present invention. The air cleaner X1 comprises a hollow cylindrical housing 10, a fan 11, a UV lamp 12, and photocatalyst granules 13.

The housing 10 is made of plastic or metal, and has an intake opening 10a and an exhaust opening 10b. The intake opening 10a is blocked off by a dust filter 14. The exhaust opening 10b is blocked off by a filter 15 through which the photocatalyst granules 13 cannot pass. The interior of the housing 10 is divided by a mesh screen 16 into a fan chamber R1 and an air cleaning chamber R2. The mesh screen 16 has an opening size small enough that the photocatalyst granules 13 cannot pass through. The fan chamber R1 accommodates the fan 11. The air cleaning chamber R2 accommodates the UV lamp 12 and the photocatalyst granules 13. A light reflecting film for reflecting and more effectively utilizing the UV rays from the UV lamp 12 may be provided to all or part of the inner wall surface of the housing 10.

The fan 11 serves to draw air from outside the apparatus to the inside, and is driven by a specific drive mechanism (not shown). This drive mechanism is accommodated along with the fan 11 in the fan chamber R1, for example.

The UV lamp 12 serves to emit UV rays in the wavelength region of less than 400 nm (such as 340-380 nm), and is disposed on the axis Y of the cylindrical housing 10. The UV lamp 12 is controlled by a specific control mechanism (not shown) including an inverter. This control mechanism is accommodated along with the fan 11 and the fan drive mechanism in the fan chamber R1, for example.

The photocatalyst granules 13 are composed of carrier particles and a photocatalytic substance fixed to these particles. The carrier particles are composed, for example, of foamed polystyrene or polyethylene terephthalate (PET), and have an average size of 0.5-10 mm, for example. The carrier particles may be shaped such that they have a plurality of tiny protrusions. Such a shape is favorable in terms of achieving a large surface area for the carrier particles. In this embodiment, the photocatalytic substance is titanium-modified calcium hydroxyapatite (Ti—CaHAP), which is a photocatalytic apatite, and/or anatase titanium oxide. The photocatalytic substance may be in the form of a powder or a thin film. A light reflecting film may be provided to the surface of the carrier particles. In this case, the photocatalytic substance is fixed over the light reflecting film. These photocatalyst granules 13 composed of light carrier particles and a photocatalytic substance can be made to billow up by the air flow generated by the operation of the fan 11, and exhibit their photocatalytic function when irradiated with UV rays from the UV lamp 12.

The basic skeleton of Ti—CaHAP that can be used as the photocatalytic substance in the present invention corresponds to the structure of CaHAP. CaHAP readily allows the exchange of both cations and anions, and therefore has good adsorptivity and adsorbs organic matter extremely well. In addition, it is known that CaHAP can inhibit or control the profliferation of mildew, microbes, and the like by securely adsorbing them. With Ti—CaHAP, titanium is incorporated into the apatite crystal structure in place of some of the calcium of the CaHAP, which forms in an apatite crystal structure a photocatalytic partial structure capable of exhibiting a photocatalytic function. The phrase "photocatalytic partial structure" could conceivably correspond to the structure of a metal oxide having a photocatalytic function. From the standpoint of obtaining both a photocatalytic function and excellent adsorptivity in the Ti—CaHAP, the proportion of titanium relative to the total metal atoms (calcium and titanium) included in the apatite crystal structure of the Ti—CaHAP used in the present invention preferably lies in the range of 3-11 mol %. Specifically, the value of Ti/(Ti+Ca) is preferably from 0.03-0.11 (molar ratio).

When Ti—CaHAP having this chemical structure is placed under UV irradiation, a synergistic effect between high adsorption strength and photocatalytic function causes it to exhibit a decomposing action that is more efficient than that of photocatalytic metal oxides, which have low adsorption strength, and in turn exhibit an efficient air cleaning action, deodorizing action, and so on.

The packing ratio of the photocatalyst granules 13 in the air cleaning chamber R2 is preferably from 50-80%, and even more preferably from 60-70%. If this packing ratio is less than 50%, the small quantity of photocatalyst granules 13 will tend to make it difficult to achieve high contact efficiency between the photocatalyst granules 13 and the air. If the packing ratio is over 80%, though, the photocatalyst granules 13 will not billow up as much, which again tends to make it difficult to achieve high contact efficiency between the photocatalyst granules 13 and the air.

To produce the photocatalyst granules 13, first, adhesive film is formed on the surface of the carrier particles by spraying a specific spray glue on the carrier particles, for example. Next, the carrier particles on the surface of which the adhesive film was formed are brought into contact with a powdered photocatalytic substance, which causes the photocatalytic substance powder to adhere to the surface of the carrier particles. The adhesive film is then dried to fix the photocatalytic substance powder to the carrier particle surface.

In another method for producing the photocatalyst granules 13, first, the surface of the carrier particles is swollen or softened by immersing the carrier particles in a specific solvent. The type of solvent is selected according to the material of the carrier particles. For instance, when the carrier particles are made from foamed polystyrene, an aromatic organic solvent such as xylene can be used as this solvent. The immersion duration is suitably determined according to the types of solvent and carrier particles. Next, a powdered photocatalytic substance is made to adhere to the carrier particle surface by bringing the carrier particles, whose surface has been swollen, into contact with the photocatalytic substance powder. The carrier particle surface is then dried to fix the photocatalytic substance powder to the carrier particle surface.

In the production of the photocatalyst granules 13, instead of using one of the above two methods, a photocatalytic substance film sputtered on a specific film may be applied to the carrier particle surface.

The filter 14 is composed of a nonwoven cloth, for example, and has a specific opening size for trapping dust and the like in the air.

The filter 15 is composed of a nonwoven cloth, for example, and has a specific opening size small enough that the photocatalyst granules 13 cannot pass through.

The mesh screen 16 is composed of a metal screen, for example, and has a specific opening size small enough that the photocatalyst granules 13 cannot pass through.

During operation of the air cleaner X1, as shown in FIG. 3, turning on the fan 11 causes air to flow through the intake opening 10a and into the air cleaner X1, pass through the filter 14, the fan 11, and the mesh screen 16, and reach the air cleaning chamber R2.

In the air cleaning chamber R2 the air comes into contact with the photocatalyst granules 13, which are agitated by the flow of the air. At this point the operation of the UV lamp 12 causes the photocatalyst granules 13 to be irradiated with UV rays, so any pollutants, microbes, or the like in the air come into contact with the photocatalyst granules 13 and are subjected to the decomposing action thereof. When Ti—CaHAP is employed for the photocatalyst granules 13, the excellent adsorptivity thereof affords a powerful decomposing action.

The air that has undergone cleaning in the air cleaning chamber R2 is exhausted from the air cleaner X1 through the exhaust opening 10b.

Since the photocatalyst granules 13 billow up as a result of the air flow during operation of the air cleaner X1, the UV rays evenly hit the entire surface of the photocatalyst granules. Accordingly, the photocatalytic function of the photocatalytic substance fixed to the photocatalyst granules 13 is fully manifested. If a light reflecting film has been provided to the inner wall surface of the housing 10, the UV rays will be reflected by the inner wall surface, which allows the UV rays to be utilized more effectively. Similarly, if a light reflecting film has been provided to the photocatalyst granules 13, the UV rays will be scattered by the photocatalyst granules 13, which again allows the UV rays to be utilized more effectively.

With the air cleaner X1, since it is granules (the photocatalyst granules 13) that perform the air cleaning function, the contact efficiency between the photocatalytic substance and the air per unit of volume is high. Accordingly, the air cleaner X1 is suited to setting the air cleaning function per unit of volume higher. The air cleaning function or photocatalytic function per unit of volume can be adjusted by suitably adjusting the particle size or surface area of the photocatalyst granules and the packing ratio of the photocatalyst granules in the vessel. The motion or billowing of the photocatalyst granules can be suitably adjusted by adjusting the mass and shape of the photocatalyst granules and the packing ratio of the photocatalyst granules in the vessel.

With the air cleaner X1, the air cleaning chamber R2 has a cylindrical shape having a main extension direction, and the UV lamp 12 extends along the axis Y of this cylindrical shape. Accordingly, during operation of the UV lamp 12, as shown in FIG. 4, the UV lamp 12 emits UV rays radially from the axis Y of the air cleaning chamber R2. This uniform UV radiation in the air cleaning chamber R2 is favorable in terms of evenly irradiating with UV rays the individual photocatalyst granules 13 that are billowing due to the air flow.

Figure 5:
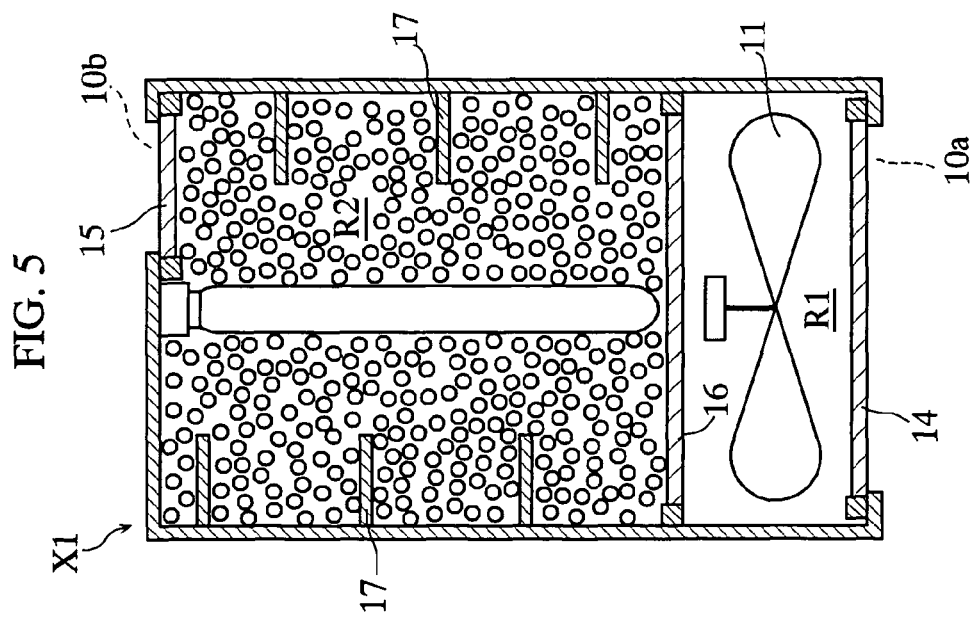
FIG. 5 illustrates a modification of the air cleaner shown in FIG. 1.
Figure 7:
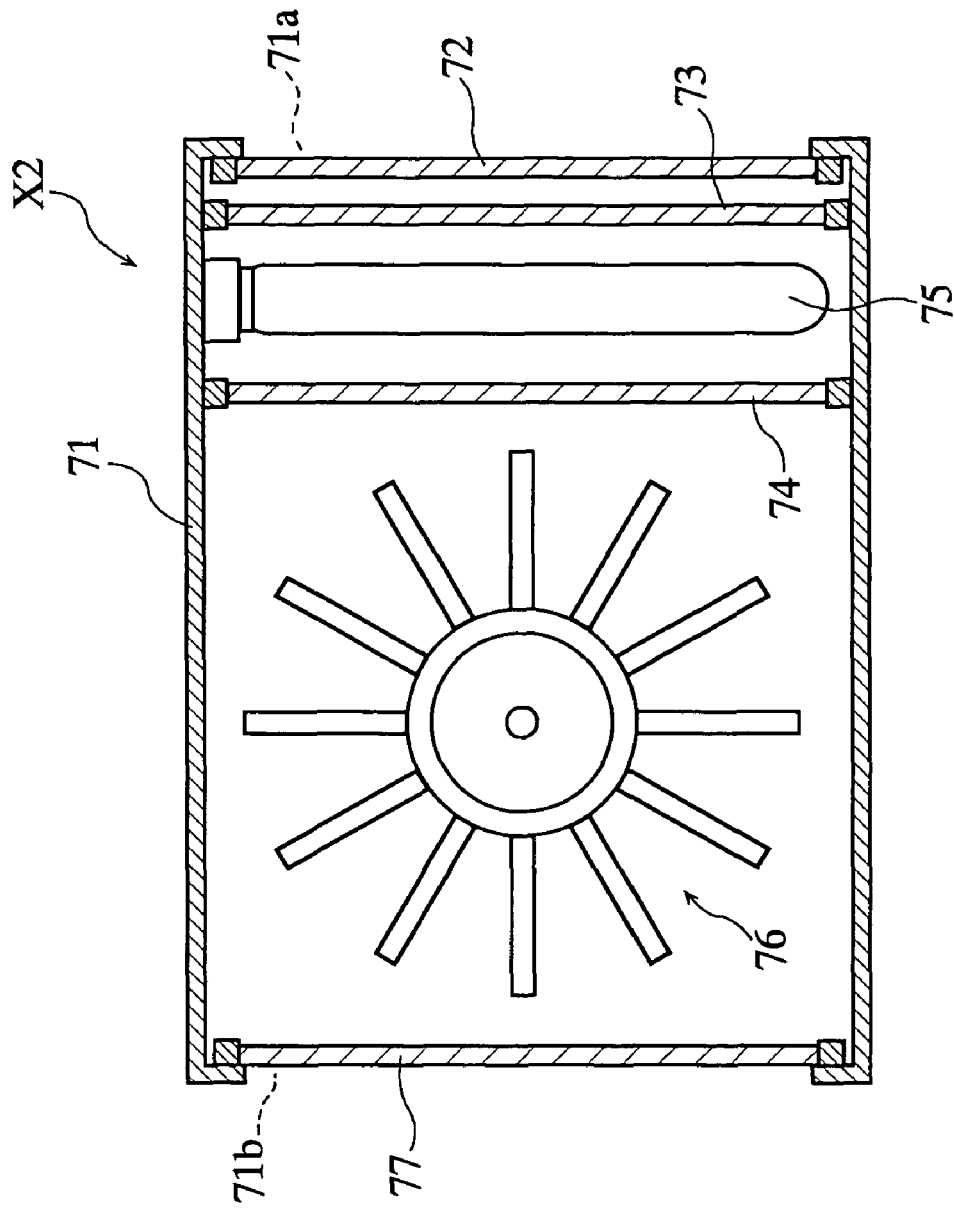
FIG. 7 is a cross section of a conventional air cleaner that utilizes a photocatalytic substance.

In the present invention, the baffles 17 shown in FIG. 5 may be provided on the inside of the air cleaning chamber R2. The baffles 17 are substantially rectangular in shape, for example, and are provided perpendicular to the inner wall surface of the housing 10. By obstructing the linear air flow, these baffles 17 serve to generate a turbid air flow in the air cleaning chamber R2. The shape of the baffles 17 may be different from that shown in FIG. 5. When baffles 17 are thus provided, the agitation or billowing of the photocatalyst granules 13 is promoted during operation of the apparatus. As a result, this tends to increase the contact efficiency between the photocatalyst granules 13 and the air.

EXAMPLES

Production of Photocatalyst Granules 0.1 g of Ti—CaHAP powder (used as photocatalytic apatite; average secondary particle size: 5.7 μm, titanium content: 10 mol %) was uniformly made to adhere and fixed to the surface of 1 g of foamed polystyrene beads (average particle size: 5 mm).

More specifically, first, 500 g of an aqueous dispersion containing 20% photocatalytic apatite (made by Meisei) was mixed with 200 g of an acrylic resin-based binder (trade name: TASRESIN UND-A, made by Bayer). Next, a photocatalytic apatite coating solution was prepared by diluting this liquid mixture with water so that the final volume was 1 L. Foamed polystyrene beads were then immersed in this coating solution. The foamed polystyrene beads were then lifted out of the coating solution and then put in a dryer (100° C.) and dried by being allowed to stand for 1 minute. This produced photocatalyst granules.

<Measuring of Photocatalytic Function>

An air cleaner having the structure shown in FIG. 1 was produced using the photocatalyst granules obtained as above, and the air cleaning function of this air cleaner was examined.

The air cleaning chamber of the apparatus in this working example was defined by a cylindrical wall having a diameter of 100 mm and a height of 200 mm (inside dimensions). A black light (trade name: FL10BLB (10 W), made by Toshiba) was used as the UV lamp. A cooling fan (trade name: SanAce 120L DC fan motor, made by Sanyo Electric) was used for the fan. The packing ratio of photocatalyst granules in the air cleaning chamber was 50%.

In the measurement of the air cleaning function, an apparatus readied as discussed above was placed in a test chamber (1 $m^3$ volume) and the fan of the apparatus was actuated, which drew air into the vessel at a rate of 4 $m^3$/min. The test chamber had been filled with acetaldehyde with a concentration of 50 ppm. The apparatus was operated for 3 hours, and the acetaldehyde concentration was measured at 30-minute intervals. As a result, it was confirmed that the acetaldehyde concentration steadily decreased. It was also confirmed that the concentration of the carbon dioxide (gas) produced by the decomposition of the acetaldehyde steadily increased as the acetaldehyde concentration went down. FIG. 6 is a graph of the measurement results. In FIG. 6, the vertical axis is the ratio of the measured concentration versus the initial acetaldehyde concentration, as well as the measured carbon dioxide concentration, while the horizontal axis is the elapsed time. Curve A in FIG. 6 is the change over time in the acetaldehyde concentration, while curve B is the change over time in the carbon dioxide concentration. It can be seen from FIG. 6 that the acetaldehyde is suitably decomposed by the air cleaner of this working example.

The invention claimed is:

1. An air cleaner comprising:
a cleaning chamber through which air can pass;
an ultraviolet light source provided in the cleaning chamber;
an air flow generator to generate an air flow in the cleaning chamber by passing air through the cleaning chamber; and
photocatalyst granules including a photocatalytic apatite, held in the cleaning chamber, and displaceable by the air flow;
wherein a packing ratio of the photocatalyst granules in the cleaning chamber is 50-80%;
wherein the photocatalytic apatite has a chemical structure in which part of calcium of calcium hydroxyapatite has been replaced with titanium;
wherein the photocatalyst granules include carrier particles and the photocatalytic apatite fixed on the carrier particles;
wherein the carrier particles are composed of a foamed resin; and
wherein the carrier particles each having a surface formed with a light reflecting film, and the photocatalytic substance is fixed over the light reflecting film.

2. The air cleaner according to claim 1, wherein the packing ratio of the photocatalyst granules in the cleaning chamber is 60-70%.

3. The air cleaner according to claim 1, wherein the cleaning chamber is columnar in shape, having a main extension direction, and the ultraviolet light source extends axially in the main extension direction of this columnar shape.

4. The air cleaner according to claim 3, wherein the cleaning chamber is cylindrical in shape.

5. The air cleaner according to claim 1, further comprising a dust filter through which air passes prior to flowing into the cleaning chamber.

6. The air cleaner according to claim 1, further comprising turbulence generation means in the cleaning chamber.

* * * * *